(12) United States Patent
Pusateri (10) Patent No.: US 10,842,940 B1
(45) Date of Patent: Nov. 24, 2020

(54) ADHESIVE THUMB RING AND SYRINGE ASSEMBLY, AND AN ADHESIVE THUMB RING FOR A SYRINGE

(71) Applicant: Todd Christopher Pusateri, Fort Lauderdale, FL (US)

(72) Inventor: Todd Christopher Pusateri, Fort Lauderdale, FL (US)

(*) Notice: Subject to any disclaimer, the term of this patent is extended or adjusted under 35 U.S.C. 154(b) by 83 days.

(21) Appl. No.: 15/592,547

(22) Filed: May 11, 2017

Related U.S. Application Data (60) Provisional application No. 62/334,496, filed on May 11, 2016.

(51) Int. Cl.
*A61M 5/31* (2006.01)
*A61M 5/315* (2006.01)

(52) U.S. Cl.
CPC ...... *A61M 5/3137* (2013.01); *A61M 5/31511* (2013.01); *A61M 2005/3139* (2013.01); *A61M 2005/3142* (2013.01); *A61M 2202/0007* (2013.01)

(58) Field of Classification Search
CPC ........ A61M 5/3137; A61M 2005/3139; A61M 2005/3142; A61M 5/31511; A61M 2205/073; A61M 2205/075
See application file for complete search history.

(56) References Cited

U.S. PATENT DOCUMENTS

| | | | |
|---|---|---|---|
| 1,832,533 A | 11/1931 | Creasy | |
| 2,842,128 A * | 7/1958 | Hein, Jr. ................. | A61M 5/31 604/227 |
| 3,118,447 A * | 1/1964 | Hunt ................... | A61M 5/31511 604/227 |
| 4,217,896 A | 8/1980 | Behnke | |
| 4,351,334 A * | 9/1982 | Inglefield, Jr. ...... | A61M 5/3148 604/227 |
| 4,687,472 A | 8/1987 | Gross | |
| 5,246,011 A * | 9/1993 | Caillouette ........ | A61B 10/0283 600/566 |
| 5,485,853 A * | 1/1996 | Stubbs ............... | A61B 10/0045 600/565 |
| 6,086,569 A | 7/2000 | Schweizer | |
| 6,669,672 B2 | 12/2003 | Wu | |
| 6,764,471 B2 | 7/2004 | Lee | |
| 9,901,686 B2 * | 2/2018 | Morgan ............. | A61M 5/3202 |
| 2009/0270050 A1 * | 10/2009 | Brown ..................... | A45F 5/00 455/90.3 |
| 2011/0196313 A1 * | 8/2011 | Mudd ................ | A61M 5/31511 604/219 |

(Continued)

*Primary Examiner* — Quynh-Nhu H. Vu
(74) *Attorney, Agent, or Firm* — John Rizvi; John Rizvi, P.A.—The Patent Professor (57) ABSTRACT

An adhesive thumb ring for a syringe is provided including a ring body and an adhesive surface on the ring body. The adhesive surface is configured to adhere to a plunger head on a syringe barrel of a syringe. For instance, the adhesive thumb ring can be rapidly and securely attached to a curved, T-shaped plunger head of a typically pre-filled, pre-packaged dermal filler syringe. The adhesive thumb ring is particularly suitable for facilitating one-handed pushing and pulling operation of the syringe in the injection of dermal filler into the skin of a patient, significantly assisting the syringe operator in preventing vascular occlusion.

12 Claims, 5 Drawing Sheets

(56) References Cited

U.S. PATENT DOCUMENTS

| | | | |
|---|---|---|---|
| 2012/0220948 A1* | 8/2012 | Barbour | A61M 5/3137 604/189 |
| 2013/0061990 A1* | 3/2013 | Syma | A45C 11/182 150/137 |
| 2013/0146625 A1* | 6/2013 | Karle | A45F 5/00 224/217 |
| 2014/0219411 A1* | 8/2014 | Dederer | G21D 3/06 376/299 |
| 2016/0213570 A1* | 7/2016 | Athanassiou | A61J 7/0053 |
| 2018/0078705 A1* | 3/2018 | Alamat | A61M 5/3137 |

* cited by examiner

ADHESIVE THUMB RING AND SYRINGE ASSEMBLY, AND AN ADHESIVE THUMB RING FOR A SYRINGE

CROSS-REFERENCE TO RELATED APPLICATIONS

This application claims the benefit of U.S. Provisional Patent Application Ser. No. 62/334,496, filed on May 11, 2016, which is incorporated by reference herein in its entirety.

FIELD OF THE INVENTION

The present invention relates generally to medical devices, and more particularly, to an adhesive thumb ring which is attachable to a syringe plunger to facilitate one-handed pushing and pulling of the syringe plunger such as for a process of injecting a dermal filler into a person's skin in cosmetic remediation applications.

BACKGROUND OF THE INVENTION

Injectable dermal fillers are soft tissue fillers which are injected into the skin to fill in facial wrinkles and restore a smoother, more youthful appearance to the skin. A dermal filler is typically injected under the skin using a syringe.

In executing the injection of the dermal filler under the skin using a syringe, the operator of the syringe must be careful to avoid injecting the filler material into a blood vessel in the skin, as it could clog the blood vessel (i.e. cause vascular occlusion) and cause necrosis of the skin. Furthermore, if a substance is injected into a blood vessel, an adverse reaction may result in the patient.

In order to prevent vascular occlusion, syringe operators typically insert the syringe needle into the skin and carry out a checking procedure before injecting the dermal filler material to ensure that the needle has not been inserted into a blood vessel. The checking procedure consists in pulling on the syringe plunger with one hand while holding the syringe barrel with the other hand. If the pulling of the plunger causes entry of blood into the syringe barrel, it may be concluded that the needle has been inserted into a blood vessel, and therefore, needs to be repositioned. On the other hand, if blood does not enter the syringe barrel, it may be concluded that the needle is correctly placed, and thus the syringe operator can proceed with injecting the filler into the skin without the risk of clogging the blood vessel.

Conventional syringes which are used to inject dermal fillers into skin are typically difficult to operate. These syringes require a clumsy, two-handed technique for operation, and more particularly to carry out the checking procedure described heretofore, in order to guarantee that the needle is correctly inserted without the risk of causing a vascular occlusion. Moreover, the needle tip can become displaced during execution of the pulling and pushing process described above. Patient discomfort increases with clumsy needle movement. Additionally, the two-handed technique prolongs the time which is required to complete the procedure.

Accordingly, there is an established need for an injecting device which facilitates injection of a dermal filler into skin in cosmetic remediation applications, and more particularly helps reduce the risk of causing vascular occlusion.

SUMMARY OF THE INVENTION

The present invention is directed to an adhesive thumb ring which can be attached to a syringe plunger to facilitate pulling the plunger in addition to pushing the plunger. The adhesive thumb ring may be used in a variety of applications. For instance and without limitation, the adhesive thumb ring can attach to a conventional, typically curved T-shaped head provided in the plunger of existing pre-filled, pre-packaged dermal filler syringes. Applying the adhesive thumb ring to the plunger head facilitates one-handed injection of a dermal filler into skin in cosmetic remediation applications. The adhesive thumb ring may be suitable for syringes having a syringe barrel, a syringe needle extending from the syringe barrel, a sliding syringe plunger in the syringe barrel and a plunger flange terminating the syringe plunger. The adhesive thumb ring may include an annular ring body having an interior surface and an exterior surface. An adhesive strip having an adhesive surface may be provided on the exterior surface of the ring body. A detachable adhesive strip cover may be provided on the adhesive surface of the adhesive strip. Accordingly, the ring body of the thumb ring may be attached to the plunger flange on the syringe plunger by detaching the adhesive strip cover from the adhesive surface of the adhesive strip. The adhesive surface of the adhesive strip may be pressed against the plunger flange on the plunger of the syringe. Thus, the operator of the syringe can extend the thumb through the ring body of the adhesive thumb ring and grasp the plunger flange with the index and middle fingers of the same hand. The adhesive surface on the ring body of the thumb ring may be configured to generate a sufficiently strong bond with the plunger head such that the bond can generate a pulling force on the plunger head that is capable of overcoming an internal vacuum force inside the syringe barrel of the syringe and allow pulling of the syringe plunger by pulling of the thumb body ring. Thus, the syringe operator can both pull and push the plunger in the syringe barrel, using one hand only.

In a first implementation of the invention, an adhesive thumb ring and syringe assembly includes a syringe and an adhesive thumb ring. The syringe has a syringe barrel and a syringe plunger movably attached to the syringe barrel and protruding outward of the syringe barrel through a proximal end of the syringe barrel. The syringe plunger is selectively movable a first direction towards an internal space of the syringe barrel and an opposite, second direction outward of the internal space of the syringe barrel. The adhesive thumb ring, in turn, includes a ring body having an interior surface and an exterior surface, and an adhesive material on the exterior surface. The ring body is shaped and sized for the insertion therethrough of a person's thumb. The syringe and the adhesive thumb ring are configured to adopt a first configuration in which the syringe and the adhesive thumb ring are detached from one another. The syringe and the adhesive thumb ring can alternatively adopt a second configuration in which the ring body is attached to the syringe plunger by an adherence of the adhesive material of the adhesive thumb ring to an outer surface of the syringe plunger.

In a second aspect, the adhesive thumb ring and syringe assembly can further include a needle carried by the syringe barrel at a distal end thereof. The needle is in fluid communication with the internal space of the syringe barrel.

In another aspect, in the first configuration, a cover can be removably attached to, and conceal, the adhesive material of the adhesive thumb ring. The cover is removed from the adhesive thumb ring to switch the syringe and the adhesive thumb ring to the second configuration.

In another aspect, the ring body can be deformable. In the second configuration, the ring body can be deformed to conform to a shape of the outer surface of the syringe plunger.

In another aspect, the syringe plunger can include a plunger head arranged at a proximal end of the syringe plunger, wherein the plunger head provides the outer surface to which the adhesive thumb ring is adhered.

In yet another aspect, the plunger head can be formed with a curved T-shape.

In another aspect, the assembly can be configured to adopt a pushing configuration in which the syringe and the adhesive thumb ring are in the second configuration and the ring body and syringe plunger are moving towards the syringe barrel by a force being exerted on the ring body in the first direction. Alternatively, the assembly can adopt a pulling configuration in which the syringe and the adhesive thumb ring are in the second configuration and the ring body and syringe plunger are moving away from the syringe barrel by a force being exerted on the ring body in the second direction.

In another aspect, the ring body can be closed and curved. For instance, the ring body can be circular, oval or elliptical.

In another aspect, the ring body can have a width of ¾" to 1".

In another implementation of the invention, an adhesive thumb ring and syringe assembly includes a syringe and an adhesive thumb ring. The syringe comprises a syringe barrel and a syringe plunger movably attached to the syringe barrel and protruding outward of the syringe barrel through a proximal end thereof. The syringe barrel has a syringe flange extending transversely at the proximal end of the syringe barrel. The syringe plunger is selectively movable in a first direction towards an internal space of the syringe barrel, and in an opposite, second direction outward of the internal space of the syringe barrel. The adhesive thumb ring, in turn, includes a ring body having an interior surface and an exterior surface. An adhesive material is arranged on the exterior surface. The ring body is shaped and sized to allow the insertion therethrough of a person's thumb. The adhesive thumb ring and syringe assembly is configured to adopt a detached configuration in which the syringe and the adhesive thumb ring are detached from one another. The adhesive thumb ring and syringe assembly can further adopt a pushing configuration in which the ring body is attached to the syringe plunger by an adherence of the adhesive material of the adhesive thumb ring to an outer surface of the syringe plunger, and in which the ring body and syringe plunger are moving towards the syringe barrel by a force being exerted on the ring body in the first direction and by the ring body pushing the syringe plunger. The adhesive thumb ring and syringe assembly can alternatively be operated to adopt a pulling configuration in which the ring body is attached to the syringe plunger by the adherence of the adhesive material of the adhesive thumb ring to the outer surface of the syringe plunger, and in which the ring body and syringe plunger are moving away from the syringe barrel by a force being exerted on the ring body in the second direction and the ring body pulling the syringe plunger.

In a second aspect, the syringe plunger can include a curved plunger head at a proximal end thereof providing the outer surface of the syringe plunger. The ring body can be deformable and can conform to a curved shape of the outer surface of the syringe plunger when the ring body is attached to the syringe plunger by the adherence of the adhesive material of the adhesive thumb ring to the outer surface of the syringe plunger.

In another implementation of the invention, an adhesive thumb ring for a syringe includes a ring body having an interior surface and an exterior surface, the ring body configured for the insertion therethrough of a person's thumb. An adhesive material is provided on the exterior surface of the ring body. The adhesive material is configured to adhere the ring body to a head of a plunger of a syringe.

In a second aspect, the adhesive thumb ring can further include an adhesive strip on the exterior surface of the ring body, wherein the adhesive material is provided on the adhesive strip.

In another aspect, the adhesive thumb ring can further include a peel-off cover covering the adhesive material.

In another aspect, the ring body can be closed and curved.

In yet another aspect, the ring body can be circular, oval or elliptical.

In another aspect, the ring body can have a width of ¾" to 1".

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward an adhesive thumb ring which is attached to a syringe plunger to facilitate one-handed pulling and pushing of a syringe plunger when carrying out an injection of a dermal filler into skin in cosmetic remediation applications.

Referring initially to FIGS. 1 through 4, an adhesive thumb ring 100 is illustrated in accordance with an exemplary embodiment of the present invention. As shown, the adhesive thumb ring 100 includes a ring body 102. As illustrated, in some embodiments, the ring body 102 may have a circular or annular shape. In other embodiments, the ring body 102 may have alternative shapes such as, but not limited to, an ellipse, an oval or other similarly closed, preferably curved shape. The ring body 102 may be fabricated of plastic, cardboard, lightweight metal or other suitable material which is consistent with the functional requirements of the adhesive thumb ring 100. In some embodiments, the ring body 102 may have a width or diameter which is about ¾" to about 1". In other embodiments, the ring body 102 may have alternative sizes.

Figure 1:
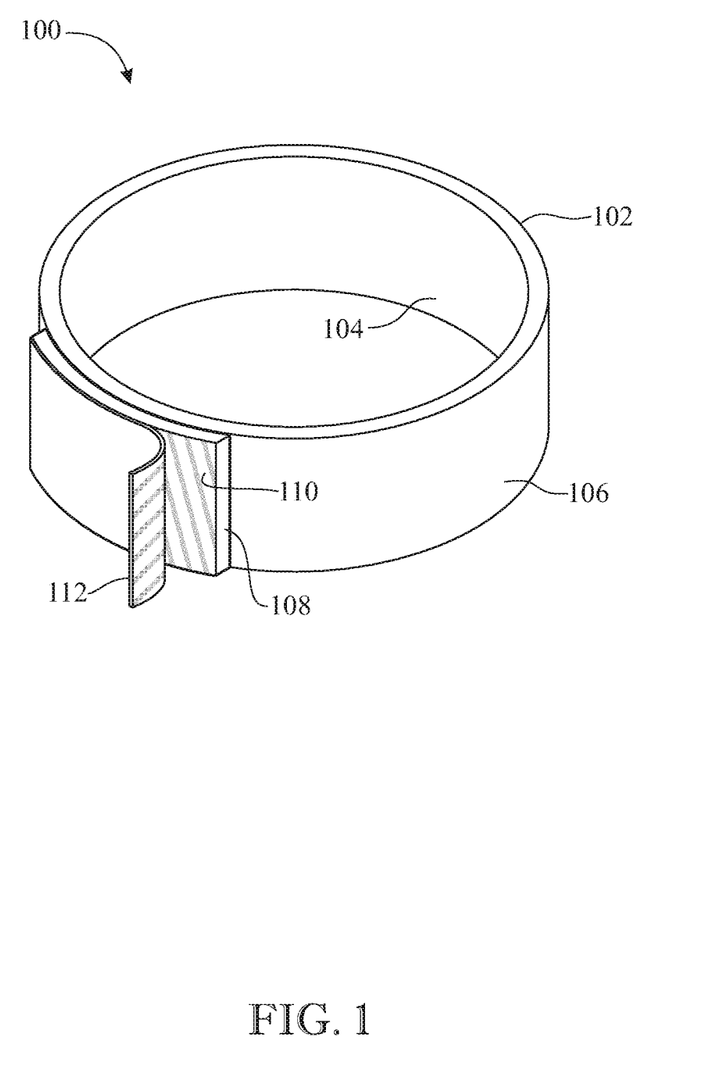
FIG. 1 presents a perspective view of an adhesive thumb ring for a syringe in accordance with a first exemplary embodiment of the present invention.

As illustrated in FIG. 1, the ring body 102 may have an interior surface 104 and an exterior surface 106. The interior surface 104 and exterior surface 106 of the present embodiment are cylindrical in shape. An adhesive strip 108 may be provided on the exterior surface 106 of the ring body 102. The adhesive strip 108 may have an adhesive surface 110 on an outer side thereof, comprising an adhesive material. A peel-off, adhesive strip cover 112 may initially adhere to the adhesive surface 110. Preparatory to use of the adhesive thumb ring 100, the adhesive strip cover 112 may be selectively peeled from the adhesive surface 110 to expose the adhesive surface 110.

In some embodiments, the adhesive strip 108 may be made of paper, plastic or another support material provided with adhesive on opposite sides, wherein one side is adhered to the exterior surface 106 of the ring body 102 and the other side provides the adhesive surface 110. In other embodiments, the adhesive strip 108 may be integrally formed with the ring body 102, the outer side of the adhesive strip providing the adhesive surface 110. In other embodiments, the adhesive strip 108 may be a layer of adhesive material, adhered to the exterior surface 106 of the ring body 102 and having an outer surface providing the adhesive surface 110.

Figure 2:
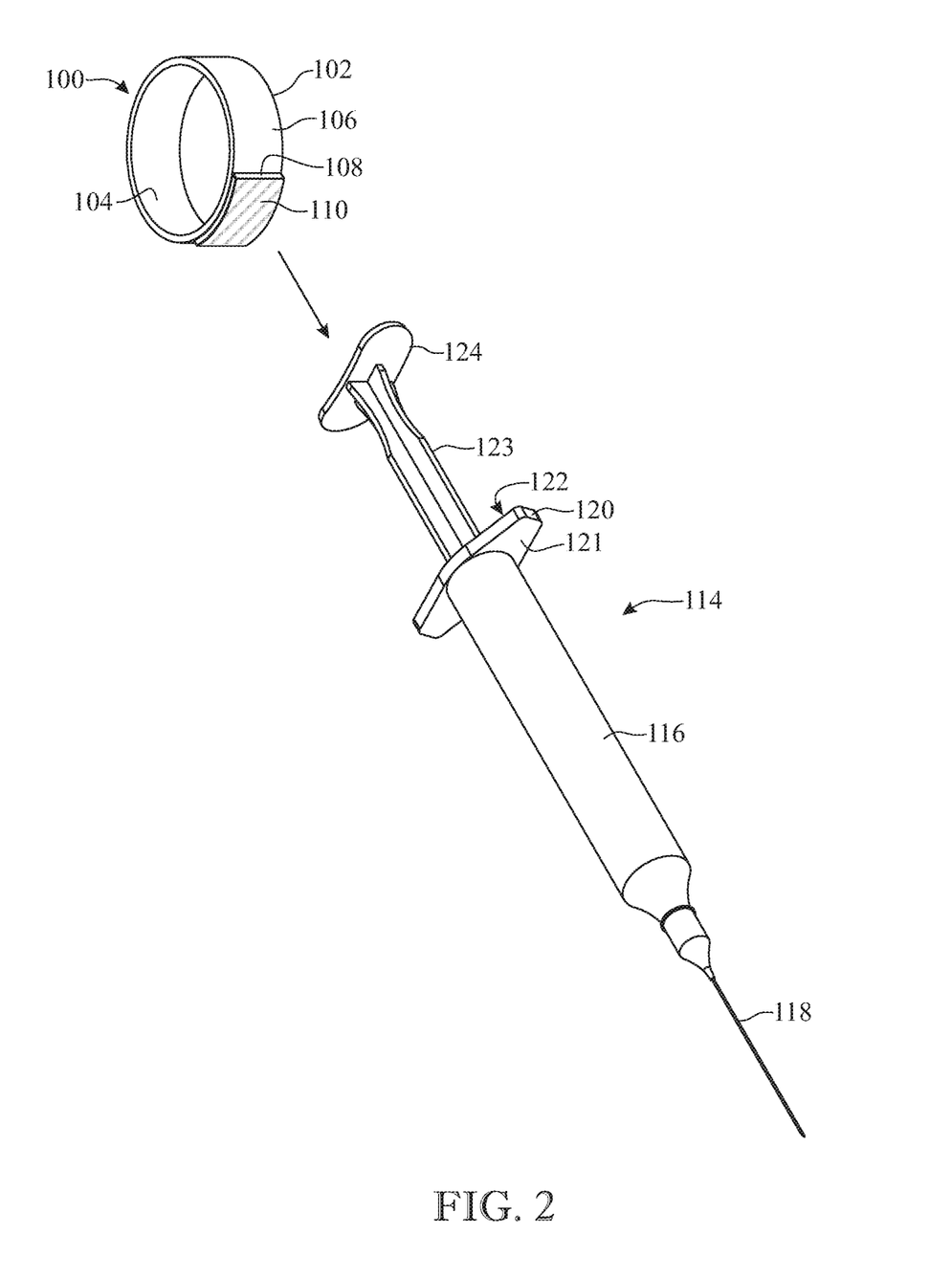
FIG. 2 presents a perspective view of the adhesive thumb ring of FIG. 1 being attached to an exemplary dermal filler kit syringe provided with a plunger ending in a curved, T-shaped plunger head.
Figure 3:
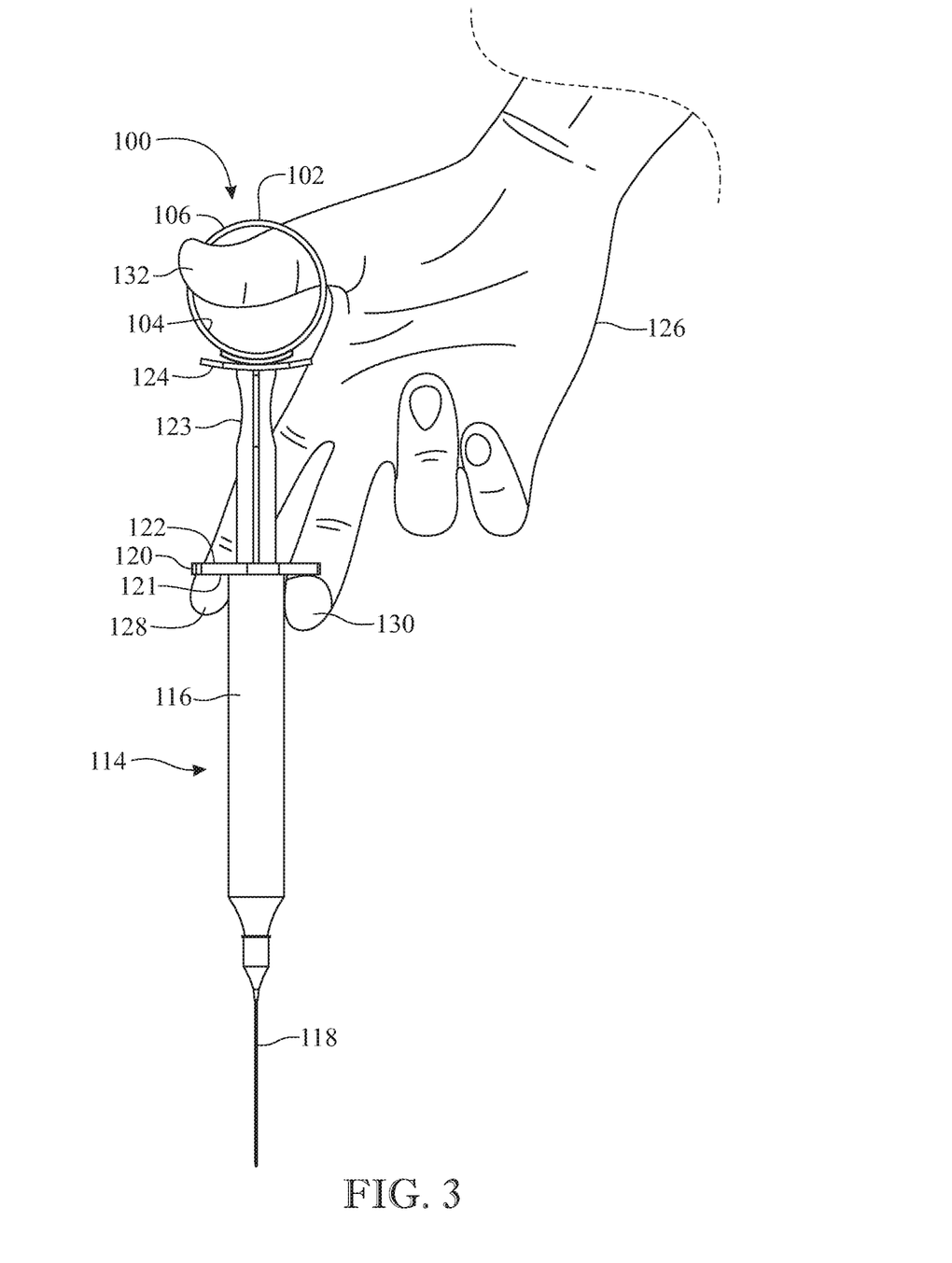
FIG. 3 presents a front elevation view of the syringe and adhesive thumb ring of FIG. 2 being operated by a syringe operator in typical application of the adhesive thumb ring.
Figure 4:
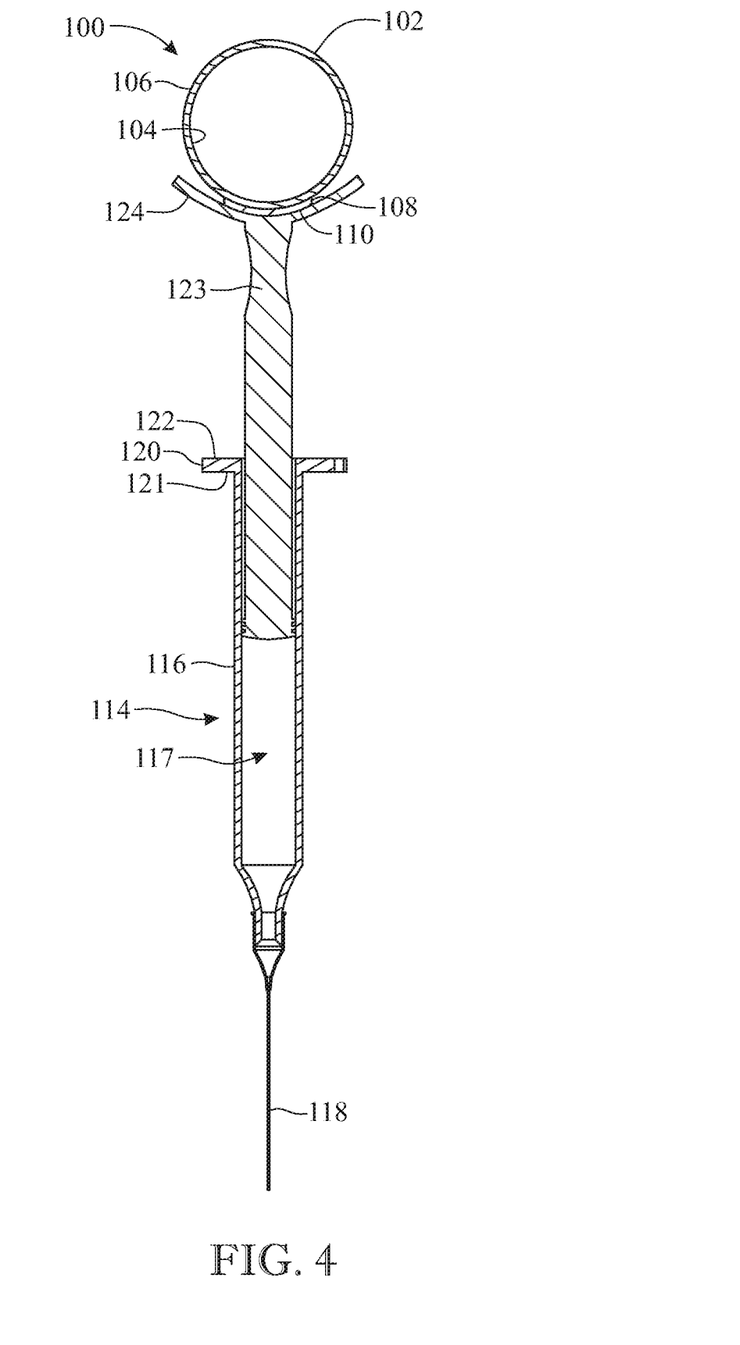
FIG. 4 presents a cross-sectional front elevation view of the syringe and adhesive thumb ring of FIG. 2, shown attached.

As illustrated in FIGS. 2-4, in typical application, the adhesive thumb ring 100 may be attached to and used in conjunction with a syringe 114 to facilitate one-handed operation of the syringe 114. The syringe 114 may have a conventional design with an elongated syringe barrel 116 defining an internal space 117. A syringe needle 118 may extend from a distal end of the syringe barrel 116, in fluid communication with the internal space 117 of the syringe barrel 116. A syringe flange 120 may terminate a proximal end of the syringe barrel 116. The syringe flange 120 has a front side 121 and a rear side 122. A sliding syringe plunger 123 may be disposed in the syringe barrel 116, slidable along the internal space 117. A plunger head 124 may terminate the end of the syringe plunger 123 which extends outside the syringe plunger 123. The plunger head 124 depicted herein is curved and T-shaped, as is typical in dermal filler application syringes.

As illustrated in FIGS. 2 and 4, the adhesive thumb ring 100 may be attached to the plunger head 124 of the syringe plunger 123 by first detaching the adhesive strip cover 112 from the adhesive surface 110 on the adhesive strip 108, as illustrated in FIG. 1. As illustrated in FIG. 2, the adhesive surface 110 may next be firmly pressed against the plunger head 124 of the syringe plunger 123, thereby creating an adhesive bond between the adhesive surface 110 and the plunger head 124, which attaches the adhesive thumb ring 100 to the syringe plunger 123. In some embodiments, the ring body 102 and adhesive strip 108 of the adhesive thumb ring 100 can be slightly deformable, such that the adhesive thumb ring 100 is deformed to conform to the shape of the plunger head 124 when the adhesive surface 110 is pressed against the plunger head 124, to increase the adhesive surface area between the adhesive thumb ring 100 and the plunger head 124. The adhesive bond between the adhesive surface 110 and the plunger head 124 can be sufficiently strong to maintain the adhesive thumb ring 100 in the deformed shape, conforming to the shape of the plunger head 124. Further, the adhesive material of the adhesive surface 110 is selected and configured to generate a sufficiently strong adhesive bond between the ring body 102 and the plunger head 124 such that the adhesive bond can generate a pulling force on the plunger head 124 that is capable of overcoming an internal vacuum force inside the syringe barrel 116 and facilitate pulling of the syringe plunger 123 by pulling the adhesive thumb ring 100 in the direction away from the syringe barrel 116.

As illustrated in FIG. 3, in typical application, a syringe operator or user may wish to use a syringe 114 as described hereinabove for any applicable use. For instance and without limitation, the syringe operator may wish to use the syringe 114 for carrying out a process of injecting a supply of dermal filler into the skin (not illustrated) of a patient. The injected dermal filler may fill in facial wrinkles in the skin, restoring a smoother and more youthful appearance.

In order to facilitate the process, the user may attach the adhesive thumb ring 100 to the syringe 114. More specifically, the ring body 102 of the adhesive thumb ring 100 can be adhesively secured to the plunger head 124 of the syringe plunger 123, typically as was heretofore described with respect to FIGS. 1 and 2. Next, the thumb 132 on a hand 126 of the syringe operator may be extended through the ring body 102. The index finger 128 and middle finger 130 on the same hand 126 of the syringe operator may grasp the syringe flange 120 on the syringe 114. As shown in FIG. 3, the user's index finger 128 and middle finger 130 may specifically rest on the front side 121 of the syringe flange 120 in order to facilitate pushing the syringe plunger 123; alternatively, the user's index finger 128 and middle finger 130 may rest on the rear side 122 of the syringe flange 120 in order to facilitate pulling the syringe plunger 123.

The syringe operator may insert the syringe needle 118 into a medical vial (not illustrated) which contains a supply of the dermal filler. While resting the index finger 128 and middle finger 130 on the rear side 122 of the syringe flange 120, the syringe operator can move the thumb 132 away from the syringe plunger 123 to pull the adhesive thumb ring 100. Pulling of the adhesive thumb ring 100 causes a pulling of the plunger head 124, via the adhesive bond between the adhesive thumb ring 100 and the plunger head 124. Thus, the syringe plunger 123 is displaced outward from within the syringe barrel 116, creating a depression in the internal space 117 of the syringe barrel 116. The pressure decrease draws the dermal filler from the medical vial through the syringe needle 118 and into the syringe barrel 116. After the syringe barrel 116 has received the desired quantity of dermal filler and the syringe needle 118 is withdrawn from the medical vial and is ready to be inserted into the patient's skin. Alternatively, in some applications, the syringe barrel 116 of the syringe 114 may be pre-filled with a selected quantity of the dermal filler prior to attachment of the adhesive thumb ring 100 to the plunger head 124.

The syringe operator then inserts the syringe needle 118 into the skin of the patient. After the syringe needle 118 is inserted into the patient's skin, the user may again rest the index finger 128 and middle finger 130 on the rear side 122 of the syringe flange 120 and move the thumb 132 away from the syringe plunger 123 to pull the adhesive thumb ring 100, thus pulling the syringe plunger 123 to partially withdraw the syringe plunger 123 from the syringe barrel 116. This action may withdraw a small quantity of fluid from the patient's skin through the syringe needle 118 into the syringe barrel 116. In the event that the fluid which is drawn into the syringe barrel 116 includes blood, the syringe operator may conclude that the syringe needle 118 has been inserted into a blood vessel in the patient's skin. Accordingly, the syringe operator may slightly withdraw and reposition the syringe needle 118 and repeat the process until the fluid which is drawn from the patient's skin is clear and no longer includes blood. When blood is not detected, the syringe operator may conclude that the syringe needle 118 has not been inserted into a blood vessel in the patient's skin. Then, the syringe operator can rest the index finger 128 and middle finger 130 on the front side 121 of the syringe flange 120 and push the thumb 132 forward against the interior surface 104 of the ring body 102 to displace the syringe plunger 123 in the syringe barrel 116 of the syringe 114. This action causes the syringe plunger 123 to increase the pressure in the syringe barrel 116, forcing the dermal filler from the syringe barrel 116 through the syringe needle 118 and into the patient's skin. The syringe operator may subsequently repeatedly withdraw the syringe needle 118 from the patient's skin, obtain another quantity of the dermal filler from the medical vial and again inject the dermal filler into the patient's skin, as was heretofore described, to inject the selected quantity of dermal filler and impart the desired appearance to the patient's skin. After use, the adhesive thumb ring 100 may be detached from the plunger head 124 of the syringe plunger 123 and preferably discarded.

While a dermal filler application has been described as way of example, it will be recognized and understood by those skilled in the art that the syringe 114, with the adhesive thumb ring 100 attached to the plunger head 124, may have a variety of alternative uses.

Figure 5:
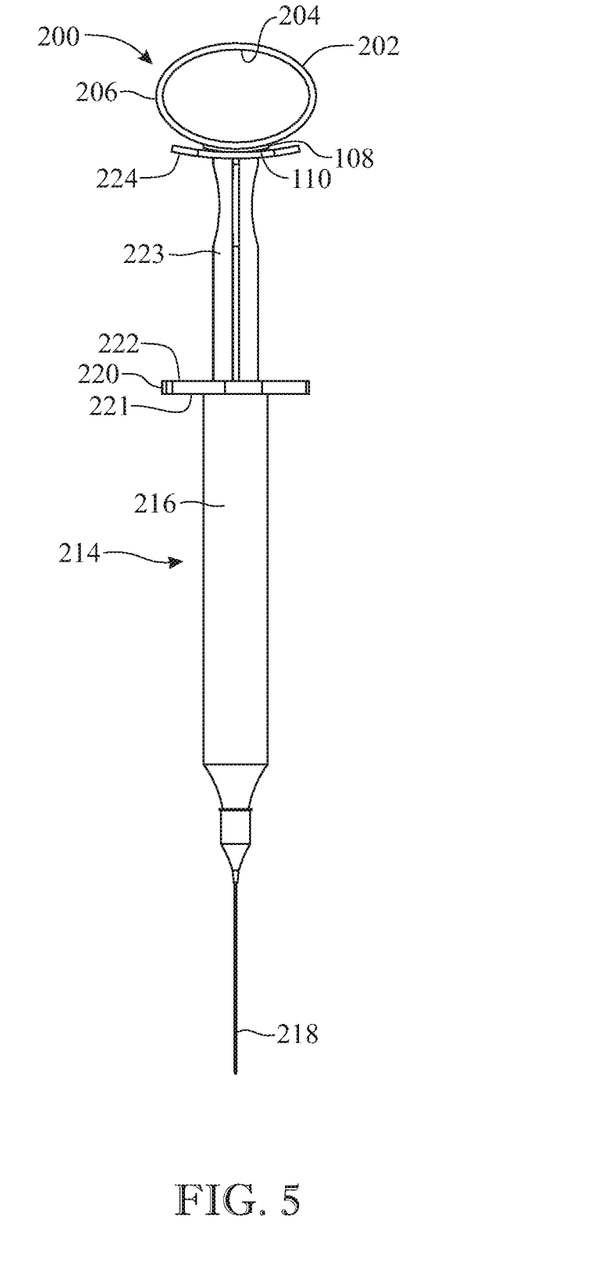
FIG. 5 presents a front elevation view of an adhesive thumb ring in accordance with a second exemplary embodiment of the invention, shown attached to a syringe.

Referring next to FIG. 5, an alternative illustrative embodiment of the adhesive thumb ring is generally indicated by reference numeral 200. The adhesive thumb ring 200 may have a design which is the same as or similar to that of the adhesive thumb ring 100 heretofore described with respect to FIGS. 1-4, with like reference numerals in the 200 series corresponding to like reference numerals of the adhesive thumb ring 100 in the 100 series. The adhesive thumb ring 200 may have a generally elongated, oval or elliptical shape. Operation of the adhesive thumb ring 200 may be as was heretofore described with respect to the adhesive thumb ring 100. Accordingly, the adhesive thumb ring 200 may be configured to more closely engage the thumb 132 (FIG. 3) on the hand 126 of the syringe operator to further facilitate pushing and pulling of the adhesive thumb ring 200.

It will be appreciated by those skilled in the art that the adhesive thumb rings of the disclosure allow a syringe operator to operate a syringe both in the normal manner by pushing on the syringe plunger using the thumb and also pulling on the syringe plunger using the same thumb. The adhesive thumb rings are easy to place on the syringe, facilitate easy one-handed operation to facilitate dermal filler injection, quickly allow a syringe operator to check placement of the syringe needle tip and avoid blood vessel occlusion, expedite dermal filler placement, reduce procedure completion time and increase patient comfort.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An adhesive thumb ring and syringe assembly, comprising:
   a syringe, comprising a syringe barrel and a syringe plunger movably attached to the syringe barrel and protruding outward of the syringe barrel through a proximal end thereof, wherein the syringe plunger is selectively movable in a first direction towards an internal space of the syringe barrel and in an opposite, second direction outward of the internal space of the syringe barrel; and
   an adhesive thumb ring formed as a separate piece relative to the syringe, the adhesive thumb ring comprising:
      a deformable ring-shaped body configured for the insertion therethrough of a person's thumb, the ring-shaped body defined by a concave interior surface and a convex exterior surface,
      an adhesive material along the convex exterior surface of the ring-shaped body, the adhesive material defining an outer, convex adhesive surface, and
      a peel-off cover covering the convex adhesive surface of the adhesive material; wherein
   the syringe and the adhesive thumb ring are configured to adopt:
      an initial, first configuration, in which the syringe and the adhesive thumb ring are detached from one another and the peel-off layer covers the convex adhesive surface of the adhesive material of the adhesive ring,
      a second configuration, in which the peel-off cover is peeled off of the convex adhesive surface of the adhesive material of the adhesive ring and the ring shaped body is attached to the syringe plunger by an adherence of the convex adhesive surface of the adhesive material of the adhesive thumb ring to an outer surface of the syringe plunger, and
      a third configuration, achievable by pressing the ring-shaped body towards the outer surface of the syringe plunger in the second configuration, wherein, in the third configuration, the ring-shaped body and the convex adhesive surface are deformed to provide a greater contact surface area between the convex adhesive surface of the adhesive material and the outer surface of the syringe plunger than in the second configuration.

2. The adhesive thumb ring and syringe assembly of claim 1, further comprising a needle carried by the syringe barrel at a distal end thereof, wherein the needle is in fluid communication with the internal space of the syringe barrel.

3. The adhesive thumb ring and syringe assembly of claim 1, wherein, in the second configuration, the ring shaped body is deformed to conform to a shape of the outer surface of the syringe plunger.

4. The adhesive thumb ring and syringe assembly of claim 1, wherein the syringe plunger comprises a plunger head arranged at a proximal end of the syringe plunger, wherein the plunger head provides said outer surface.

5. The adhesive thumb ring and syringe assembly of claim 4, wherein the plunger head is formed with a curved T-shape.

6. The adhesive thumb ring and syringe assembly of claim 1, wherein the assembly is configured to adopt:
 a pushing configuration in which the syringe and the adhesive thumb ring are in the third configuration and the ring-shaped body and syringe plunger are moving towards the syringe barrel by a force being exerted on the ring-shaped body in the first direction, and
 a pulling configuration in which the syringe and the adhesive thumb ring are in the third configuration and the ring-shaped body and syringe plunger are moving away from the syringe barrel by a force being exerted on the ring-shaped body in the second direction.

7. The adhesive thumb ring and syringe assembly of claim 1, wherein the ring-shaped body is closed and curved.

8. The adhesive thumb ring and syringe assembly of claim 1, wherein the ring-shaped body is circular.

9. The adhesive thumb ring and syringe assembly of claim 1, wherein the ring-shaped body is oval or elliptical.

10. The adhesive thumb ring and syringe assembly of claim 1, wherein the ring-shaped body has a diameter of ¾" to 1".

11. An adhesive thumb ring and syringe assembly, comprising:
 a syringe, comprising a syringe barrel and a syringe plunger movably attached to the syringe barrel and protruding outward of the syringe barrel through a proximal end thereof, wherein the syringe plunger is selectively movable in a first direction towards an internal space of the syringe barrel and in an opposite, second direction outward of the internal space of the syringe barrel, and further wherein the syringe plunger comprises a curved plunger head at a proximal end thereof, the curved plunger head comprising a concave proximal surface; and
 an adhesive thumb ring formed as a separate piece relative to the syringe, the adhesive thumb ring comprising:
  a deformable ring-shaped body configured for the insertion therethrough of a person's thumb, the ring-shaped body having a concave interior surface and a convex exterior surface,
  an adhesive material along the convex exterior surface of the ring-shaped body, the adhesive material defining an outer, convex adhesive surface, and
  a peel-off cover covering the convex adhesive surface of the adhesive material; wherein
 the syringe and the adhesive thumb ring are configured to adopt:
  an initial, first configuration, in which the syringe and the adhesive thumb ring are detached from one another and the peel-off layer covers the convex adhesive surface of the adhesive material of the adhesive ring,
  a second configuration, in which the peel-off cover is peeled off of the convex adhesive surface of the adhesive material of the adhesive ring and the ring-shaped body is attached to the concave proximal surface of the curved plunger head by an adherence of the convex adhesive surface of the adhesive material of the adhesive thumb ring to the concave proximal surface, and
  a third configuration, achievable by pressing the ring-shaped body towards the concave proximal surface of the curved plunger head in the second configuration, wherein, in the third configuration, the ring-shaped body and the convex adhesive surface are deformed to provide a greater contact surface area between the convex adhesive surface of the adhesive material and the concave proximal surface of the curved plunger head than in the second configuration.

12. An adhesive thumb ring and syringe assembly, comprising:
 a syringe, comprising a syringe barrel and a syringe, plunger movably attached to the syringe barrel and protruding outward of the syringe, barrel through a proximal end thereof, wherein the syringe plunger is selectively movable in a first direction towards an internal space of the syringe barrel and in an opposite, second direction outward of the internal space of the syringe barrel, and further wherein the syringe plunger comprises a curved plunger head at a proximal end thereof, the curved plunger head comprising a concave proximal surface; and
 an adhesive thumb ring formed as a separate piece relative to the syringe, the adhesive thumb ring comprising:
  a deformable ring-shaped body configured for the insert on therethrough of a person's thumb, the ring-shaped body having a concave interior surface and a convex exterior surface,
  an adhesive strip along the convex exterior surface of the ring-shaped body, the adhesive strip defining an outer, convex adhesive surface, and
  a peel-off cover covering the convex adhesive surface of the adhesive strip; wherein the syringe and the adhesive thumb ring are configured to adopt:
  an initial, first configuration, in which the syringe and the adhesive thumb ring are detached from one another and the pee-off layer covers the convex adhesive surface of the adhesive strip of the adhesive ring,
  a second configuration, in which the peel-off cover is peeled off of the convex adhesive surface of the adhesive strip of the adhesive ring and the ring-shaped body is attached to the concave proximal surface of the curved plunger head by an adherence of the convex adhesive surface of the adhesive strip of the adhesive thumb ring to the concave proximal surface, and
  a third configuration, achievable by pressing the ring-shaped body towards the concave proximal surface of the curved plunger head in the second configuration, wherein, in the third configuration, the ring-shaped body and the convex adhesive surface are deformed to provide a greater contact surface area between the convex adhesive surface of the adhesive strip and the concave proximal surface of the curved plunger head than in the second configuration.

* * * * *